United States Patent [19]
Sims et al.

[11] Patent Number: 6,107,543
[45] Date of Patent: *Aug. 22, 2000

[54] CULTURE OF TOTIPOTENT EMBRYONIC INNER CELLS MASS CELLS AND PRODUCTION OF BOVINE ANIMALS

[75] Inventors: Michelle M. Sims, Stoughton; Neal L. First, Madison, both of Wis.

[73] Assignee: Infigen, Inc., DeForest, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/348,769

[22] Filed: Dec. 2, 1994

Related U.S. Application Data

[63] Continuation of application No. 07/932,451, Aug. 20, 1992, abandoned.

[51] Int. Cl.[7] ........................... C12N 15/09; C12N 15/00; C12N 5/00; C12N 15/63
[52] U.S. Cl. ................................ 800/21; 800/15; 800/17; 800/24; 435/373; 435/325; 435/378; 435/379; 435/380; 435/381; 435/455; 435/449; 435/450; 435/375; 435/377; 435/383; 435/392
[58] Field of Search ................................... 800/2, 15, 24, 800/8, 21; 435/325, 375, 377, 383, 392, 172.3, 172.1, 172.2, 455, 449, 450; 935/93, 102, 106, 107, 52

[56] References Cited

U.S. PATENT DOCUMENTS

| | | | |
|---|---|---|---|
| 4,994,384 | 2/1991 | Prather et al. | 435/172.2 |
| 5,096,822 | 3/1992 | Rosenkrans, Jr. | 435/240.1 |
| 5,120,657 | 6/1992 | McCabe et al. | 435/287 |

FOREIGN PATENT DOCUMENTS

| | | |
|---|---|---|
| WO 09/03432 | 4/1990 | WIPO. |
| 9013627 | 11/1990 | WIPO. |

OTHER PUBLICATIONS

Webster's II: New Riversid University Dictionary. Houghton Mifflin Co., MA 1988. p. 273.
Stedman's Medical Dictionary, 24th Edition. Williams & Wilkins, Baltimore. p. 289, 1982.
A. Bradley et al. BioTechnol. 10: 534–8 ('92).
B. Stanton et al. Brain Pathol. 2: 71–83 ('92).
H. Baribault et al. Mol. Biol. Med. 6 :481–92 ('89).
M. Frohman et al. Cell 56 : 145–7 ('89).
A. Van Stekelenburg–Hamess et al. Mol. Rep. & Dev. 40(4) 444–54 ('95) (Abstract).
M. Sims et al. PNAS 91 : 6143–7 ('92).
Van Brunt, J. Bio Technology, vol. 6, #10,(1988) pp. 1149–1154.
Balakier , H., et al. Developmental Biology, vol. 113 (1986) pp. 155–159.
Graham, C.F., 1969, "The Fusion of Cells with One and Two Cell Mouse Embryos," *Wistar Inot. Symp Monogr.,* 9:19.
Modlinski, J.A., et al., 1990, "Nuclear Transfer from Teratocarcinoma Carcinoma Cells into Mouse Oocytes and Eggs," *Development,* 108:337–348.
Moreau, J. F., et al., 1988, "Leukaemia–inhibiting Factor is Identical to the Myeloid Growth Factor, Human Interleukin for DA Cells," *Nature, Lond.* 336: 690–692.
Nagy, A., et al., 1990, "Embryonic Stem Cells Alone Are Able to Support Fetal Development in the Mouse," *Development,* 110:815–821.
Notarianni, E., et al., 1991, "Derivation of Pluripotent, Embryonic Cell Lines from the Pig and Sheep," *J. Reprod. Fert. Suppl.* 43:255–260.
Hassan–Hauser, C., et al., "Long Time Culture of Cattle Embryos for Establishing Totipotent Embryonic Stem Cells," *Reprod. Dom. Anim.* 25, 22–32 (1990).
Alberts, B., et al., Ed., 1989, *Molecular Biology of the Cell, Second Edition,* Garland Publishing, Inc., New York, pp. 859–863.
Anderson, G.B., 1992, "Isolation and Use of Embryonic Stem Cells from Livestock Species," *Animal Biotechnology,* 3(1), 165–175.
Butler, J.E., et al., 1987, "Production of Ovine Chimeras by Inner Cell Mass Transplantation," *J. Animal Sci.,* 65:317–324.
Capecchi, M. R., 1989a, "The New Mouse Genetics: Altering the Genome by Gene Targeting," *Trends Genet.,* 5: 70–76.
Capecchi, M. R., 1989b, "Alternating the Genome by Homologous Recombination," *Science, N Y,* 244: 1288–1292.
Collas, P. and J.M. Robl, 1991, "Relationship Between Nuclear Remodelling and Development in Nuclear Transplant Rabbit Embryos," *Biol. Reprod.,* 45:455–465.
Doetschman, T.P., et al., 1988, "Establishment of Hamster Blastocyst–Derived Embryonic Stem (ES) Cells," *Dev. Biol.,* 127:224.
Ebert, K.M. and J.P. Selgrath, 1991, "Changes in Domestic Livestock Through Genetic Engineering," *Animal Applications of Research in Mammalian Development,* 4:233–266.
Evans, M.J., et al., 1990, "Derivation and Preliminary Characterization of Pluripotent Cell Lines from Porcine and Bovine Blastocysts," *Theriogenology,* 33:125.
Evans, M.J. and M.H. Kaufman, 1981, "Establishment in Culture of Pluripotent Cells from Mouse Embryos," *Nature,* 292:154.
First and Prather, 1991, "Genomic Potential in Mammals," *Differentiation,* 48:1–8.

(List continued on next page.)

*Primary Examiner*—Jasemine Chambers
*Assistant Examiner*—Jill D. Martin

[57] ABSTRACT

The use of totipotent embryonic stem cells to provide substantially identical cells for embryo cloning techniques is described. The method includes the culture of loose suspensions of inner cell mass cells of bovine animals to retrieve large populations of stem cells. The invention also describes the use of stem cells in various genetic manipulation techniques.

6 Claims, 4 Drawing Sheets

OTHER PUBLICATIONS

Gossler, A., et al., 1986, "Transgenesis by Means of Blastocyst–Derived Embryonic Stem Cell Lines," *Proc. Natl. Acad. Sci.,* 83:9065.

Hansel, W. and R.A. Godke, 1992, "Future Prospectives on Animal Biotechnology," *Animal Biotechnology* 3(1), 111–137.

Hooper, M., et al., 1987, "HPRT–Deficient (Lesch–Nyhan) Mouse Embryos Derived from Germ Line Colonization by Cultured Cells," *Nature,* 326:292.

Illmensee, K. and P.C. Hoppe, 1981, "Nuclear Transplantation in *Mus musculus*: Developmental Potential of Nuclei from Preimplantation Embryos," *Cell,* 23:9–18.

Joyner, A.L., 1991, "Gene Targeting and Gene Trap Screens Using Embryonic Stem Cells: New Approaches to Mammalian Development," *Bioassays,* 13(12):649–658.

Kim, T., 1992, "A study of Retrovirus–Mediated Gene Transfer in Bovine Embryos," Ph.D. Thesis, University of Wisconsin–Madison.

Koller, B.H., et al., 1989, "Germ Line Transmission of a Plasmid Alteration Made in a Hypoxanthine Phosphoriboxyl Transferase Gene by Homologous Recombination in Embryonic Stem Cells," *Proc. Natl. Acad. Sci.,* 86:8927.

Kono, T., et al., 1991, "Development of Enucleated Mouse Oocytes Reconstituted with Embryonic Nuclei," *J. Reprod. Fert.,* 93:165–172.

Lovell–Badge, R.H., et al., 1987, "Tissue Specific Expression of the Human Type II Collagen Gene in Mice," *Proc. Natl. Acad. Sci.,* 84:2803.

McGrath, J. and D. Solter, 1983, Nuclear Transplantation in the Mouse Embryo by Microsurgery and Cell Fusion, *Science,* 220:1300.

Navara, C.S., et al., 1992, Timing of Polarization in Bovine Embryos and Developmental Potential of Polarized Blastomeres (Abst. 82), *Soc. Study of Reprod.—Suppl. 1,* 46:71.

Notarianni, E., et al., 1990, "Derivation of Pluripotent Embryonic Cell Lines from Porcine and Ovine Blastocysts," Proc. 4th World Cong. Genetics Applied to Livestock Production XIII, 58–64.

Notarianni, E., et al., 1990, "Maintenance and Differentiation in Culture of Pluripotential Embryonic Cell Lines from Pig Blastocysts," *J. Reprod. Fert., Suppl.* 41:51–56.

Piedrahita, J.A., et al., 1988, "Isolation of Embryonic Stem Cell–Like Colonies from Porcine Embryos," *Theriogenology,* 29:286.

Prather, R.S. and J.M. Robl, 1991, "Cloning by Nuclear Transfer and Embryo Splitting in Laboratory and Domestic Animals," *Animal Applications of Research in Mammalian Development,* 4:205–232.

Rexroad, C., 1992, "Transgenic Technology in Animal Agriculture," *Animal Biotechnology,* 3(1), 1–13.

Rossant, J. & A. L. Joyner, 1989, "Towards a Molecular Genetic Analysis of Mammalian Development," *Trends Genet.,* 5: 277–283.

Saito, S., et al., 1992, "Bovine Embryonic Stem Cell–Like Cell Lines Cultured Over Several Passages," *Roux's Arch. Dev. Biol.,* 201:134–141.

Smith, A.G., et al., 1988, Inhibition of Pluripotent Embryonic Stem Cell Differentiation by Purified Polypeptides, *Nature,* 336:688.

Smith, L.C. and I. Wilmut, 1989, "Influence of Nuclear and Cytoplasmic Activity on the Development in vivo of Sheep Embryos after Nuclear Transplantation," *Biol. Reprod.,* 40:1027–1035.

Stanton, B.R., et al., 1990, Germ–Line Transmission of an Inactive N–myc Allele Generated by Homologous Recombination in Mouse Embryonic Stem Cells, *Mol. Cell. Biol.,* 10:6755.

Stewart, C. L., 1991, "Prospects for the Establishment of Embryonic Stem Cells and Genetic Manipulation of Domestic Animals," *Animal Applications of Research in Mammalian Development,* Cold Spring Harbor Laboratory Press, New York, pp. 267–283.

Summers, P.M., et al., 1983, "Synthesis of Primary Bos taurus–Box Indicus Chimaeric Calves," *Animal Reprod. Sci.,* 6:91–92.

Williams, R.L., et al., 1988, "Myeloid Leukemia Inhibitory Factor Maintains the Developmental Potential of Embryonic Stem Cells," *Nature,* 336:684.

Wilmut, I., et al., 1991, "Genetic Manipulation of Mammals and its Application in Reproductive Biology," *J. Reprod. Fert.,* 92:245–279.

Wilmut, I., et al., 1992, "Sources of Totipotent Nuclei Including Embryonic Stem Cells," *Proc. Symp. Cloning Mammals by Nuclear Transplantation,* 8–16.

Yagi, T., et al., 1990, "Homologous Recombination at c–fyn Locus of Mouse Embryonic Stem Cells with Use of Diphtheria Toxin A Fragment Gene in Negative Selection," *Proc. Natl. Acad. Sci.,* 87:9918.

CULTURE OF TOTIPOTENT EMBRYONIC INNER CELLS MASS CELLS AND PRODUCTION OF BOVINE ANIMALS

This is a continuation of application Ser. No. 07/932,451 filed Aug. 20, 1992, now abandoned.

FIELD OF THE INVENTION

The present invention is generally directed to genetically manipulated embryos and specifically to the culture of totipotent embryonic stem cells to provide substantially identical cells for use in genetic manipulation techniques to produce large populations of clonal offspring.

REFERENCE CITATIONS

The section preceding the claims is a bibliography of the references cited in this application.

DESCRIPTION OF THE PRIOR ART

Techniques for genetically improving animals are continually being sought. In the not-too-distant past, the primary method of improving desired characteristics in animals was through selective breeding, a slow and tedious process. It is now possible to increase the speed of this process by introducing new genetic information directly into the embryos through genetic manipulation. It has also become an accepted practice to transplant embryos in animals to aid in the production of genetically superior stock. The cloning of embryos together with the ability to transplant the cloned embryo makes it possible to produce multiple genetically identical animals. Nuclear transplantation from a multi-cell embryo to a plurality of embryonic single cells enables the production of large numbers of identical animals. Reference is made to U.S. Pat. No. 4,994,384 to Prather et al., which is incorporated herein by reference, for a description of this technique.

In domestic animals such as cattle, an embryo at the 32-cell stage is called a morula. After the morula stage, an internal intercellular space enlarges to create a central fluid-filled cavity known as the blastocoel. At this stage, the embryo becomes known as a blastocyst. The cells of the blastocyst form a spherical shell having an outer cell layer known as the trophoblast or trophectoderm. One pole of the blastocyst is distinguished by a thicker accumulation of cells, known as the inner cell mass (ICM), inside the trophectoderm. The embryo is derived from the ICM, while the cells of the trophectoderm are the precursor of extraembryonic tissues and the placenta. Reference is made to Navara et al. (1992) for a more detailed description of this development.

Donor embryos at the blastocyst stage of development can be used for cloning as long as significant cell differentiation has not occurred. In the ICM of a later stage embryo, for example, the cells are totipotent; that is, they may not have undergone significant cellular differentiation, whereas the outer cells have differentiated to form the trophectoderm and are not suitable for use in embryonic cloning processes (Navara et al., 1992; Collas and Robl, 1992).

The cells of the ICM are known as stem cells. They have the ability to proliferate in an undifferentiated state as well as give rise to differentiated products. Embryonic stem (ES) cells are stem cells which have been isolated from the ICM. The isolation and multiplication in culture of totipotent ES cells have value in providing a large population of identical cells for use by nuclear transfer to produce clonal offspring (First and Prather, 1991).

Nuclear transfer of nuclei from murine ICM stem cells into enucleated oocytes was performed by Illmensee and Hoppe (1981) and Kono et al. (1991) with only limited success and in the bovine by Saito et al. (1992) with no development past the 8 cell stage and no evidence of totipotency. Smith and Wilmut (1989) disclosed the electrofusion-mediated nuclear transplantation of sheep embryos in which uncultured single stem cells derived from the ICM of early blastocyst stage sheep embryos were fused to unfertilized enucleated secondary oocytes.

Totipotent ES cells also provide a mechanism for gene transfer by transfection or infection of genes into the cells (Evans and Kaufman, 1981; Gossler et al., 1986; Lovell-Badge, 1987; Joyner, 1991; Stewart, 1991). Using a selectable marker, the transgenic cells can be separated and used either by chimerization into a blastocyst or through use as donor cells in nuclear transfer to produce transgenic offspring (Hooper et al., 1987; Joyner, 1991; Stewart, 1991). Additionally, homologous recombination techniques can be used with cultured stem cells to add or delete genes at specific sites in the genome (Koller et al., 1989; Stanton et al., 1990; Yagi et al., 1990).

To date, all of the above techniques have been accomplished only with ES cells of mice. For reviews, see Stewart, 1991, Joyner, 1991, First et al., 1991, Wilmut et al., 1991, Capecchi, 1989a, 1989b, Rossant and Joyner, 1989. Even in mice, offspring from totipotent ES cells have not been produced using conventional nuclear transfer (Modlinski et al., 1990; Anderson, 1992), although offspring were derived when murine ES cells were chimerized with tetraploid murine embryos (Nagy et al., 1990). Isolation of ES cells from Syrian golden hamster embryos has also been reported (Doetschman et al., 1988). However, hamster ES cells have not yet been shown to be capable of normal in vivo differentiation after injection into blastocysts (Anderson, 1992).

Most attempts to isolate and culture embryonic stem cells have been based on or adapted from the original methods of Martin Evans for mice (Evans and Kaufman, 1981; Evans, 1990; PCT Publication WO 09/03432 to Evans and Moor). This technique involves the separation of blastocyst ICM from trophoblast cells by immunosurgery, and culture of the intact blastocysts or ICM over a monolayer of immortal murine fibroblasts (STO cells). The putative ES cells are maintained as a colony on a monolayer of STO cells with a polypeptide purified factor from Buffalo Rat Liver (BRL)-conditioned medium, which has been reported as effective in preventing differentiation (Moreau et al., 1988; Smith et al. 1988; Williams et al., 1988). The purified factor is also known as Differentiation Inhibition Activity factor (DIA), and Leukemia-Inhibiting Factor (LIF).

While this system has allowed the culture of pluripotent cells that can become embryoid bodies with cellular beating heart activity, only in mice has it allowed the demonstration of or maintenance of totipotency of the cultured cells (reviewed by Stewart, 1991 and Anderson, 1992), and there is suggestion that these differentiation inhibiting agents do not prevent differentiation of ES cells in species other than rodents (Anderson, 1992).

The morphological identification of putative ES cells has been published for domestic animals (Piedrahita et al., 1988; Evans et al., 1990; Notarianni et al., 1990), and pluripotency has been demonstrated for stem cells of swine (Evans et al., 1990, Notarianni et al., 1990, 1991), cattle (Evans et al., 1990), and sheep (Notarianni et al., 1990), while sheep (Butler et al., 1987) and cattle (Summers et al., 1983) chimeras have been produced from injection of blastocyst ICM cells into other blastocysts.

There are no published reports indicating cultured ICM or putative ES cells of domestic species are totipotent as evidenced by late stage fetuses or offspring derived totally from ES cells (Evans, 1990; Stewart, 1991; Wilmut, 1992; Anderson 1992).

SUMMARY OF THE INVENTION

The present invention is directed to isolated cultured totipotent ES cells from domestic animals and to a process for the culture of isolated, totipotent ES cells from domestic animals that allows retrieval of large populations of ES cells and maintenance of both pluripotency and totipotency in culture. The cell culture system can be used for isolating and culturing totipotent ES cells of domestic animals, which cells can be used in genetic manipulation techniques.

The present invention is also directed to a method of culturing totipotent ES cells from domestic animals comprising isolating the inner cell mass from an embryo of a donor domestic animal, dissociating the stem cells of the inner cell mass to form dissociated ES cells, and culturing the dissociated ES cells in vitro.

The present invention is also directed to a method for transferring a nucleus from a cultured totipotent embryonic stem cell derived from an in vivo or in vitro produced embryo to a recipient oocyte and culturing the resulting nuclear transferred embryo in vitro or in vivo comprising collecting embryos from donor animals, isolating the inner cell mass from the embryos, dissociating the stem cells of the inner cell mass to form donor nuclear transfer ES cells, culturing the dissociated donor nuclear transfer ES cells, collecting and culturing recipient oocytes from donor animals or their products, enucleating the oocytes, transferring a single ES cell to the enucleated oocyte to form a nuclear transferred oocyte, and forming a viable single cell embryo from the nuclear transferred oocyte.

The present invention is also directed to blastocysts, embryos and domestic animals formed from this process.

Further, the present invention is directed to an embryonic stem cell culture medium comprising a culture solution containing the nutritional substances necessary to support an embryonic stem cell, wherein one of the nutritional substances is hemicalcium lactate in an amount effective to maintain the health and viability of the embryonic stem cell. The culture medium also includes an SIT medium, i.e., sodium selenite, insulin and transferrin, in an amount effective to support an embryonic stem cell.

The present invention is also directed to a process of introducing exogenous genetic material from a donor domestic animal to a recipient animal. The process includes collecting viable embryos either from a donor animal or in vitro derived embryos, isolating the ICM from the embryos, dissociating the stem cells of the ICM, culturing the stem cells, transforming the stem cells in vitro with the exogenous material, and introducing the transformed stem cells into the recipient domestic animal in a manner such that the exogenous genetic material is incorporated into the recipient animal's genetic structure.

The present invention marks the first demonstration of totipotency from cultured ES cells of domestic animals. The present invention also marks the first successful use of ES cells for nuclear transfer in any species.

Several features of the present invention are unique. For example, using ICM cells without segregation of the epiblast or cells presumed to have ES cell morphology has not been previously reported in domestic animals. Additionally, the successful use of a dilute suspension of ES cells in culture rather than the use of differentiation inhibitors to prevent differentiation has not been reported previously. Essentially, the culture of ES cells according to the present invention can be accomplished without requiring differentiation inhibitors.

The system of the present invention allows the retrieval of large populations of ES cells. Because ES cells proliferate rapidly in culture, a potentially inexhaustible supply of nuclear cells will become available for domestic animal embryo cloning processes. The availability of large numbers of genetically identical ES cells also enhances the opportunity to screen and select animals having desired phenotypic characteristics. Once the desired cell line is selected, the cells can be multiplied to large numbers for nuclear transfer.

The present invention is therefore particularly useful in the field of cloning embryos, especially in application to domestic animals. By use of the present methods for culturing ES cells, an entire cell line can be stored in the frozen state while progeny tests are conducted. Once it is determined that the cell line is desirable, the cell line can then be reproduced as many times as desired. This will make commercial cloning financially worthwhile.

Additionally, the expense of performing nuclear and genetic transfers is lowered. Within the cells, only the desired DNA can be transferred into the cells. With a selectable marker attached, the integrated and expressing gene can be selected. Therefore, there is a high probability of integrating the gene of choice. In nuclear transfer techniques, embryos can be made with a high probability of successful incorporation of the desired genetic structure. The embryos have the DNA integrated and a high probability of expression. Thus, the expense of performing nuclear or gene transfers in domestic animals is lowered.

Genetic screening of domestic animals is also greatly facilitated through the use of ES cells. Genetic screening involves the systematic search for certain genotypic information in animals. Genetic screening can be used to identify genetic diseases or handicaps, and it can identify animals having the ability to pass on desirable (and undesirable) phenotypic traits. Genetic markers, i. e., alleles used as a probe to mark a nucleus, chromosome or gene, have been developed in domestic species to identify animals having a variety of traits. Currently, screening is accomplished by removing cells from the developing embryo at an early stage. However, only a few cells may be removed from the embryo without destroying the embryo. Thus, only a few cells, generally no more than 4, are available for genetic screening in any embryo. On the other hand, ES cells provide the researcher with an unlimited number of cells for conducting genetic screening on an animal. Because of the diploid state of the ES cells, genetic screening can be performed at the cell level, rather than the embryo level.

Methods for transferring genes into embryos of domestic animals are also enhanced by the introduction of exogenous genetic material into cultured ES cells that are then used to form the germ cells of the embryo. For example, in cattle one of the real restrictions preventing gene transfer has been the expense of maintaining fetuses in utero. Since only 10% of the transferred offspring are expected to express desired characteristics, 90% of what is transferred is tagged a wasted effort. This results in undue expense to maintain the recipient cows. In response to this problem, the present invention provides large numbers of totipotent embryonic stem cells which can be used for gene transfer by transfection or infection of genes into cells. Homologous recombination techniques can be used with cultured stem cells to add or delete genes at specific sites in the genome.

The present invention also has advantages in nuclear transfer techniques as discussed previously. Rather than using a blastomere or nucleus from an embryo donor, an ES cell from a desired cell line is transferred into an enucleated metaphase-II oocyte, fused, developed to morula or blastocyst stage either in vivo or in vitro, and then transferred to recipient females for full development.

It is also possible to add or delete genes at specific sites in the genome utilizing the present invention. While transgenic mice with site specific gene insertion and deletion have been produced by use of homologous DNA recombination in cultured ES cells (Koller et al., 1989; Capecchi, 1989b; Stanton et al., 1990; Yagi et al., 1990), the same techniques have not heretofore been successfully accomplished in domestic animals (reviewed by Hansel and Godke, 1992; Anderson, 1992; Wilmut et al., 1991). However, ES cells cultured according to the present invention can now be used as vectors for producing the desired genetic mutations in domestic animals. By standard recombinant DNA technology, a desired mutation can be introduced into a cloned DNA sequence. The gene construct can then be transferred to the genome of the ES cells in culture. The ES cells can then be microinjected into blastocysts to produce germ line chimeras according to methods known to the art. The chimeras can then be interbred to produce animals homozygous for the desired mutation. Alternately, as shown by the present invention, the genetically modified ES cells can be used in nuclear transfer to produce offspring.

In like manner, undesired characteristics can be removed from domestic animals by microinjecting an antisense gene constructed in vitro and designed to be delivered to a target cell to regulate or inhibit a particular genetic characteristic. The net result is that very specific genetic engineering tasks can be accomplished.

Further objects, features and advantages of the present invention will be apparent from the following detailed description, drawings and the appended claims.

DETAILED DESCRIPTION OF THE INVENTION

Definitions

Figure 2:
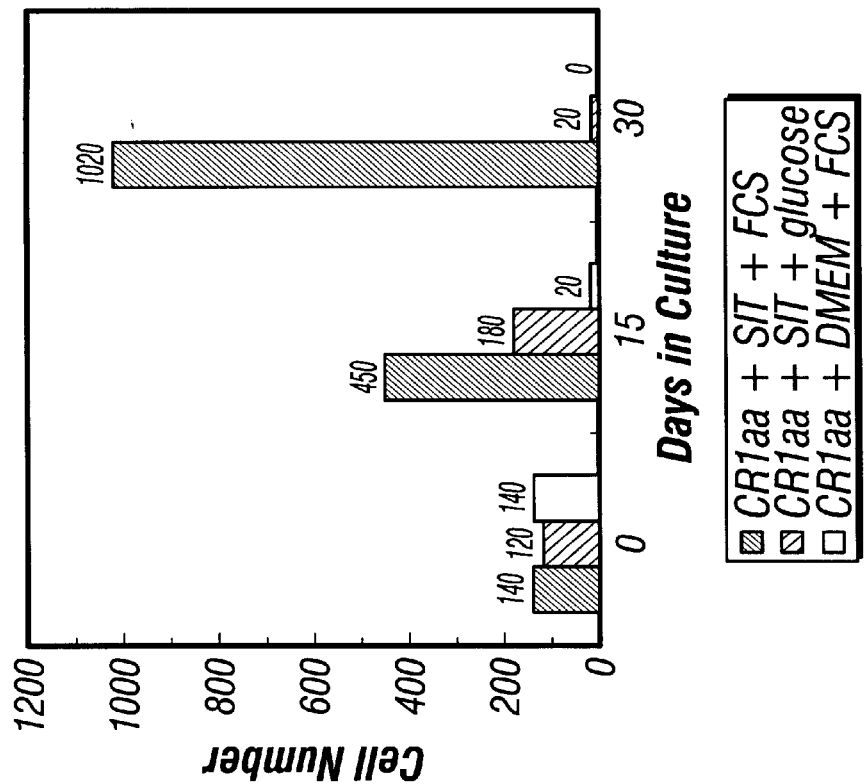
FIGS. 1–4 are tables illustrating the results of ten ES cell culture media tested for ability to maintain ES cell growth and viability after one month in culture in Experiment 1.
Figure 1:
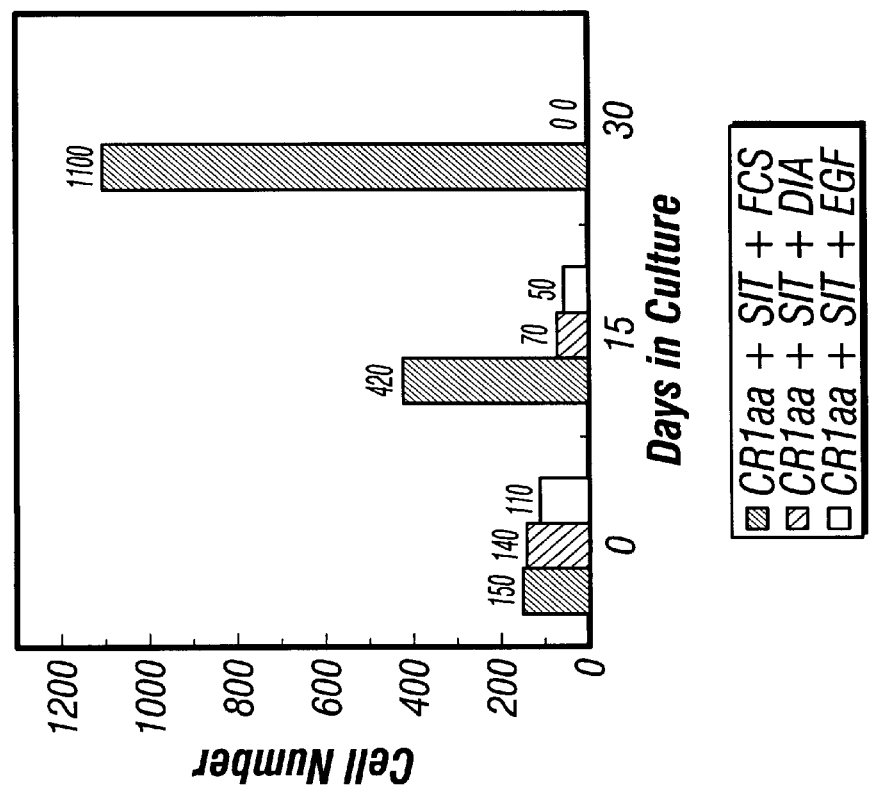
Figures 3, 4:
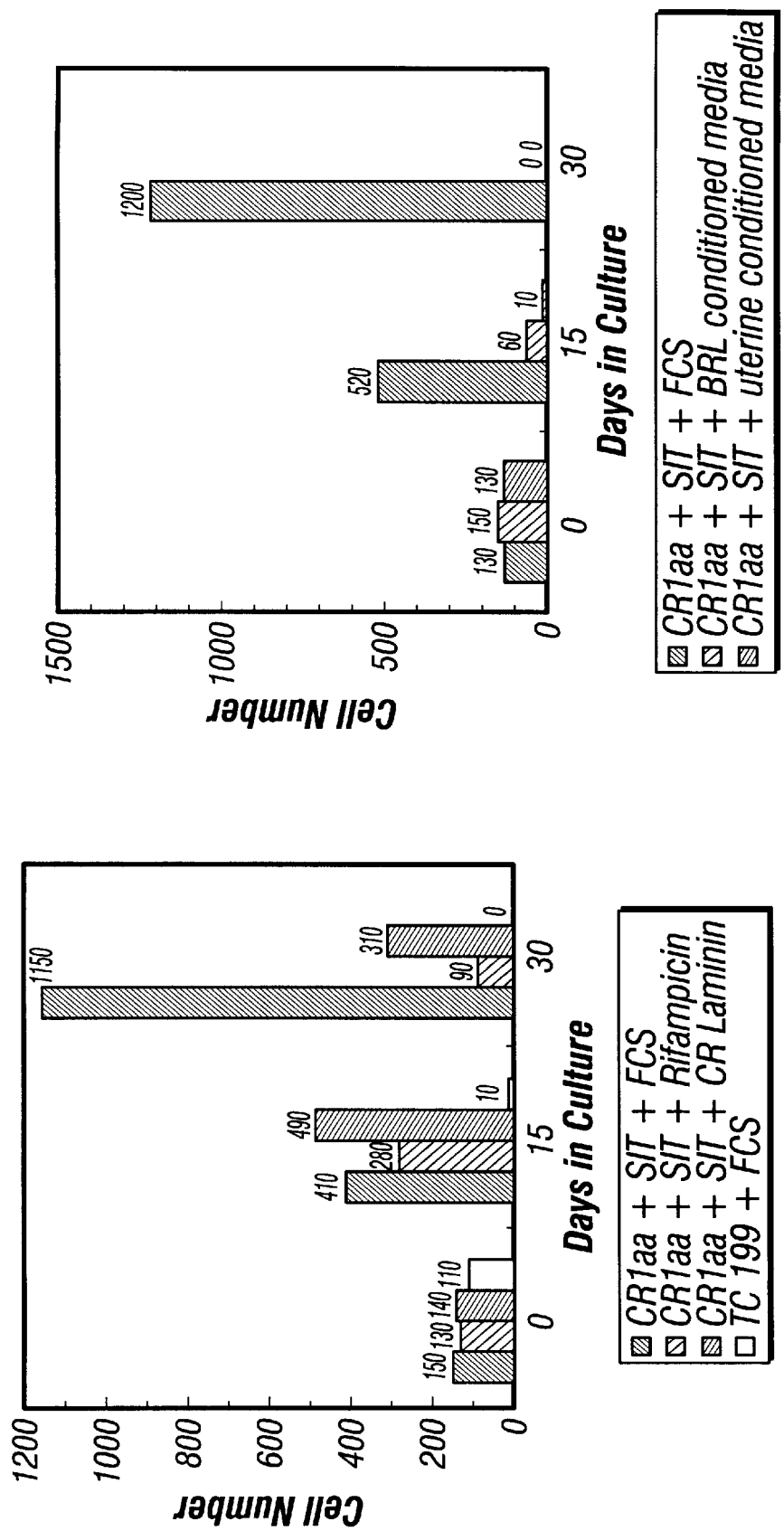

For purposes of the present invention, the following definitions will apply:

Chimera: Animals formed from aggregates of genetically different groups of cells. Chimeras can be made by injecting totipotent cells from an early embryo of one genotype into a blastocyst of another genotype, or by introducing totipotent cells into the middle of a cleavage stage embryo, i. e., an embryo having 4 or more cells. The injected cells become incorporated into the inner cell mass of the host blastocyst, and a chimeric animal develops.

Developmentally Competent Oocytes: oocytes having the ability to develop embryos.

Domestic animals: Animals generally tamed or under human control. Specifically, domestic animals refer to ruminant animals such as cattle, goats and sheep, and pseudoruminants such as horses and swine. As used in this application, the term domestic animals refers particularly to cattle.

Embryonic stem (ES) cells: The cells derived from the inner cell mass or earlier stages (i.e., morula) of the developing embryo which can be maintained in a way such that they can multiply but do not differentiate. When the cells are exposed to differentiating conditions, they are totipotent and can develop into all the tissues of the body.

Genetic manipulation: A procedure of inserting and/or deleting genes, parts of genes, fragments of DNA and/or RNA, or inserting or deleting the entire genome. Genetic manipulation includes nuclear transfer processes, gene transfer and embryo cloning.

Inner cell mass (ICM): At the early stages of development, the egg is surrounded by the zona pellucida. After fertilization, the egg cleaves to form a cluster of cells called the morula. After the 32 cell stage (in cattle), an internal cavity (blastocoel) forms and the cluster is called a blastocyst. One pole of the blastocyst has a thicker accumulation of cells, known as the inner cell mass. The entire embryo proper is derived from the inner cell mass.

Nuclear transfer or nuclear transplantation: Replacing by artificial means (micromanipulation or cell fusion) of the nucleus of one cell with that of another.

Oocyte: An egg cell which undergoes meiosis to form an ovum, i.e., an unfertilized, nonmotile female gamete, and a first polar body. Polar bodies are smaller cells that are produced during meiosis in oogenesis (the formation of an ovum) and ejected from maturing oocytes after completion of the first meiotic (reduction division) stage, also termed meiosis I. Oocyte maturation is defined as the progression of the primary oocyte through meiosis I until the development stage is arrested at the metaphase stage of meiosis II. The oocyte, now a secondary oocyte, remains in this arrested stage until fertilization triggers the completion of meiosis II (Alberts, B., et al., Ed., 1989, *Molecular Biology of the Cell, Second Edition*, Garland Publishing, Inc., New York, pp. 859–863). Therefore, the first meiotic division occurs in a primary oocyte and generates the secondary oocyte. This then undergoes the secondary meiotic division to produce the ovum.

Pluripotent stem cells: Stem cells that give rise to many cell types.

Stem cells: Cells of the inner cell mass or any other stage where they are known to be precursors to all other cell types of the body.

Totipotency: Ability of a cell to proceed through all the stages of development.

Transgenic animals: Any animal containing one or more cells bearing genetic information received, directly or indirectly, by deliberate genetic manipulation at a subcellular level, such as by microinjection or infection with recombinant virus.

The present invention lies in the culture of stem cells in a very disperse system such that the cells do not contact each other. The ICM cell culture system of the present invention prevents differentiation by culturing cells as a loose suspension. Therefore, cells are not allowed to attach to each other, which may lead to differentiation of tissue products. The stem cells cultured under the system of the present invention can be utilized as donor cells in an embryo cloning process such as the process described in the following paragraphs. Although the present invention is designed for use on a variety of domestic animals, the following description relates specifically to the bovine species.

Embryo Culture and Development

Embryos are collected either in vivo or in vitro from in vitro fertilized oocytes according to processes well known to the art. Additionally, cloned embryos may be used in the present invention. The embryos are placed in a tissue culture or maintenance medium.

There are a variety of embryo culture and maturation media routinely used for the collection and maintenance of embryos. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 MM Ma pyruvate and 50 $\mu$g/ml gentamicin sulphate. Any of the above may also involve co-culture with a variety of cell types such as granulosa cells, oviduct cells, BRL cells and uterine cells.

Another maintenance medium is described in U.S. Pat. No. 5,096,822 to Rosenkrans, Jr. et al., entitled "Bovine Embryo Medium," which is incorporated herein by reference. This embryo medium, named CR1, contains the nutritional substances necessary to support an embryo.

CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Hemicalcium L-lactate is significant in that a single component satisfies two major requirements in the culture medium: 1) the calcium requirement necessary for compaction and cytoskeleton arrangement; and 2) the lactate requirement necessary for metabolism and electron transport. Hemicalcium L-lactate also serves as valuable mineral and energy source for the medium necessary for viability of the embryos.

Advantageously, CR1 medium does not contain serum, such as fetal calf serum, and does not require the use of a co-culture of animal cells or other biological media, i.e, media comprising animal cells such as oviductal cells. Biological media can sometimes be disadvantageous in that they may contain micro-organisms or trace factors which may be harmful to the embryos and which are difficult to detect, characterize and eliminate.

Examples of the main components in CR1 medium include hemicalcium L-lactate, sodium chloride, potassium chloride, sodium bicarbonate and a minor amount of fatty-acid free bovine serum albumin (Sigma A-6003). Additionally, a defined quantity of essential and non-essential amino acids may be added to the medium. CR1 with amino acids is known by the abbreviation "CR1aa."

CR1 medium preferably contains the following components in the following quantities:

sodium chloride—114.7 mM
potassium chloride—3.1 mM
sodium bicarbonate—26.2 mM
hemicalcium L-lactate—5 mM
fatty-acid free BSA—3 mg/ml At approximately 40–48 hours post-fertilization, the embryos are stripped of all cumulus cells and extraneous sperm cells. The embryos may be stripped mechanically by pipetting the embryos through the neck of micropipette (180–210 $\mu$m inner diameter) attached to a syringe. The cumulus cells fall off and the embryos are removed from the maintenance medium. Other methods of stripping cumulus cells from the embryo include removing the cells by vortexing approximately 1 ml of the embryo medium for approximately 2–2½ minutes. Alternatively, the cells may be mechanically stripped by ultrasound techniques known to the art. The cells may also be stripped enzymatically by the application of proper enzymes such as hyaluronidase according to methods known to the art of cell culture.

Conditioning the Embryos

The embryos are conditioned in the maintenance medium under maintenance conditions until they either hatch from the zona pellucida or are fully expanded, generally 7 to 11 days at a temperature approximately 39° C. in 5% $CO_2$ in air with high humidity. The embryos are then washed and incubated, according to processes known to the art, until the stem cells are ready for removal. Embryonic stages earlier or later than the above may also be used as long as the ICM cells are not differentiated. This period encompasses the non-polarized cells of cleavage stage embryos such as morulae (Navara et al. 1992) until ICM cells differentiate after day 14.

Isolation of Inner Cell Mass

The ICM is preferably isolated from the embryo by immunosurgery of the embryo after it has been conditioned. One method of ICM isolation is as follows.

The embryos are first washed in a 3 ml $Ca^{2+}$ and $Mg^{2+}$-free TL Hepes with polyvinyl alcohol (PVA) and polyvinylpyrrolidone (PVP) solution, then washed, through 4 to 5 $CO_2$-equilibrated microdrops (50 $\mu$l of $Ca^{2+}$ and $Mg^{2+}$-free CR1aa without bovine serum albumin (BSA) and with PVA and PVP) under paraffin oil. Rabbit anti-bovine antibody (1:10 dilution, Sigma B-8270) is added at 1:10 dilution for a final concentration of 1:100. The embryos are returned to a 39° C. incubator for 30 minutes. The embryos are then again washed through 4 to 5 fresh microdrops of medium. Guinea pig complement (Sigma S-1639) is added to the embryos at 1:10 dilution from a 1:500 stock for a final dilution of 1:5000. While in the presence of complement, the zonae pellucidae are removed by manually pipetting through a non-fire polished 150$\mu$ pipette tip.

Other methods of immunosurgery using alternate antibodies, complement and different media are as effective for isolating ICMs. The only critical component is that the antibody be used in such a method to assure binding of the antibody to the trophectoderm of the embryo and the complement recognizing the antibody and binding with it to assure the destruction of the trophectoderm.

Other methods of ICM isolation may also be used. The critical aspect here involves the destruction of the trophoblast cells without damaging the inner cell mass. This can be determined by microscopic examination. There are two basic characteristics here associated with the successful development of ES cell line: (1) trophoblast destruction, and (2) maintenance of an intact ICM.

Culture of Inner Cell Mass Cells

The isolated ICMs are washed and placed in a culture medium designed to dissociate and culture viable ES cells. A preferred medium includes a culture solution containing the nutritional substances necessary to support an ES cell. One of the nutritional substances is hemicalcium lactate in an amount effective to maintain the health and viability of the ES cell. A preferred culture solution is CR1aa, described previously. Other components necessary to support the ES cell in culture include one or more of the following: SIT (a known, selenium [sodium selenite], insulin and transferrin medium), fetal calf serum (FCS) or its equivalent, DIA, epidermal growth factor (EGF), glucose, DMEM, rifampicin, CR Laminin, buffalo rat liver (BRL) conditioned medium and uterine conditioned medium (UCM). Reference is made to Experiment 1 (supra.) for a list of suitable culture media. The addition of between 5 and 50% fetal calf serum or other sera with activity similar to fetal calf serum, i.e., lamb serum and estrual cow serum is beneficial to promote viable cell growth.

Within approximately 5 days, the ICMs dissociate from aggregated masses containing many cells into smaller groups or clumps containing a few stem cells or to individual free-floating stem cells. The medium is preferably changed every 2–3 days by aspiration and replaced with fresh medium.

Maintenance of Stem Cells

The stem cells must be prevented from association and aggregation to maintain totipotency. The above culture system allows this. Modification of the above culture system can also prevent differentiation while allowing even greater mitotic activity. The stem cells may be maintained as dissociated cells in the suspension culture for extended periods up to approximately 3 months. To test pluripotency, some cell lines may be allowed to aggregate and be examined for the formation of embryoid bodies and differentiated cell types. Cell viability can be determined by staining with propidium iodide. Propidium iodide is a live/dead stain commonly used in mammalian cells. A viable cell with intact membranes excludes the stain while a dead or dying cell admits the stain and fluoresces scarlet.

At this point, stem cells from domestic animals are available for nuclear transfer, gene transfer, genetic screening and other processes.

Nuclear Transfer

The cultured non-aggregated ICM cells can be used as nuclear donor cells in nuclear transfer processes. Reference is made to Prather and Robl, 1991, which is incorporated herein by reference for a general discussion on nuclear transfer techniques.

Culture of Recipient Oocytes

For the successful commercial use of techniques such as genetic engineering, nuclear transfer or cloning, oocytes in vitro must be matured in vitro before they can be used as recipient cells for nuclear transfer or before they can be fertilized by the sperm cell to develop into an embryo. This process generally requires collecting immature (prophase I) oocytes from bovine ovaries obtained at a slaughterhouse and maturing the oocytes in a maturation medium prior to fertilization or enucleation until the oocyte enters the metaphase II stage, generally 18–24 hours post-aspiration. For purposes of the present invention, this period of time is known as the "maturation period." As used herein for calculation of time periods, "aspiration" refers to aspiration of the immature oocyte from ovarian follicles.

Alternatively, metaphase II stage oocytes, matured in vivo have been used and are found to be optimal. Mature metaphase II oocytes may be collected surgically from either nonsuperovulated or superovulated cows or heifers 35 to 48 hours past the onset of estrus or past the injection of human chorionic gonadotropin (hCG) or similar hormone.

The stage of maturation of the oocyte at enucleation and nuclear transfer is important (First and Prather, 1991). In general, successful mammalian embryo cloning practices use the metaphase II stage oocyte as the recipient oocyte. At this stage, it is believed the oocyte is sufficiently "activated" to treat the introduced nucleus as it does a fertilizing sperm. In domestic animals, and especially cattle, the oocyte activation period is between about 16–52 hours, preferably about 28–42 hours post-aspiration.

It has also been found that the rate of cumulus enclosed oocyte (CEO) development is greatly enhanced by the addition of a luteinizing hormone to the maintenance medium. Luteinizing hormone is a glycoprotein secreted by the pars distalis of the pituitary gland. In females, the hormone promotes the maturation of the Graafian follicles with the production of estrogens and is essential for ovulation and formation of the corpora lutea. For purposes of this invention, the term "luteinizing hormone" or "LH" refers to any compound with LH activity. Such compounds include naturally-derived LH, human chorionic gonadotropin (HCG) from the human placenta, and synthetic compounds expressing LH activity. The medium requires only enough LH to enhance the rate of oocyte development. Thus, LH can be included in the conditioned medium in an amount from 2 µg/ml to 10 µg/ml, and is preferably about 5 µg/ml.

Approximately 16–18 hours after the initiation of oocyte maturation, the oocytes are stripped of cumulus cells according to the processes previously described and observed for the presence of polar bodies. The importance of the observation of the polar body is explained as follows. The female gamete should have a haploid number of chromosomes before it can become fertilized.

Prior to fertilization, the female gamete must undergo reduction division to establish the proper number of chromosomes. The polar body, which develops and is ejected after completion of the first meiotic division, contains half of the chromosomes originally present in the oocyte and the remaining oocyte contains the other half. When the first polar body has been ejected, the oocyte has acquired haploid number of chromosomes which, upon fertilization with haploid sperm chromosomes, enables the formation of the diploid zygote-embryo.

In the past, it was not possible to determine the stage of oocyte development by observing the oocyte primarily because in vitro maturation required the presence of cumulus cells, which surrounded the oocyte and hid it from observation. Therefore, following the kinetics of the first polar body formation and its relation to the oocyte's developmental competence was not possible.

The requirement for a surrounding mass of cumulus cells is no longer needed. The oocyte can be seen and the presence of the first polar body can be determined.

In order for denuded bovine oocytes to mature, the maintenance medium must be conditioned. The term "conditioned," as used herein, refers to the action of the cumulus cells in the maintenance medium in order to adjust the medium to provide a desirable environment for the denuded bovine oocytes. By allowing the cumulus cells to dwell in the maintenance medium for a period of time to condition the medium, approximately two days, the medium and the cells will support maturation of denuded bovine oocytes. Because the bovine oocytes are denuded, i.e., stripped of cumulus cells, the quality of the oocytes can then be determined by the procedures described herein.

The conditioning process is as follows. Cumulus cells are stripped from an oocyte mechanically by pipetting cumulus enclosed oocytes (CEOs) through the neck of the micropipette (180–210 µm inner diameter) attached to a syringe. Cumulus cells fall off and denuded oocytes are removed from the maintenance medium. Cumulus cells are further disaggregated mechanically by pipetting them through the neck of the micropipette (20–30 µm inner diameter).

Other methods of stripping cumulus cells from an oocyte include removing the cells by vortexing approximately 1 ml of the CEO medium for approximately 2–2½ minutes. Alternatively, the cells may be mechanically stripped by ultrasound techniques known to the art. The cells may also be stripped enzymatically by the application of proper enzymes such as trypsin or collagenase according to methods known to the art of cell culture.

The medium with disaggregated cells is then placed into 5 ml of maintenance medium in a conical tube. Cells are washed twice according to the following procedure. The tube is centrifuged at 3000 rpm for 15 minutes. The supernatant is discarded and 5 ml of fresh medium is added to the pellet of cells at the bottom of the tube.

The pellet obtained after the second washing is resuspended in the maintenance medium to a final concentration of $1 \times 10^7$ cells/ml. 50 µl drops are made from the cell suspension, and covered with paraffin oil and placed in an incubator for 2–4 days (incubation conditions: 5% $CO_2$ in air, 39° C., humidified atmosphere) to form a primary cell culture layer. A primary cell culture layer is defined as a layer mostly comprising cumulus cells from the original tissue. These cells have the same functioning characteristics as cumulus cells in vivo. After two days, the drops are used for the maturation of denuded bovine oocytes.

In one embodiment, the present invention can operate as follows:

CEOs are collected from the small antral follicles from slaughterhouse bovine ovaries. The CEOs are placed in the maintenance medium and stripped from surrounding cumulus cells. A description of the stripping procedure is detailed elsewhere in this application.

Denuded oocytes are then washed twice in Hepes-buffered Tyrode medium and place in conditioned medium drops, prepared two days earlier in which a cumulus cell monolayer is formed. The oocytes are matured for approximately 16–24 hours, preferably 21 hours, at 39° C., with 5% $CO_2$ in air and maximal humidity.

Following this maturation time, the oocytes are examined microscopically (40x) for the presence of the first polar body. The oocytes which have released the first polar bodies are then considered prime candidates for fertilization. The oocytes may be fertilized in a modified tyrodes medium, known to the art, for 48 hours and placed in a culture medium for further development with extruded polar bodies by 16–18 hours have a greater developmental potential than those extruded later. The cumulus cells are a mass of somatic cells which surround the oocyte in vivo. The cumulus cells provide both protection and the nutrients needed to mature the oocyte.

Micromanipulation of Stem Cells

Micromanipulation of the stem cells is performed in a manner similar to the methods of McGrath and Solter, 1983, which is incorporated herein for details of the micromanipulation technique. Manipulation is performed in culture dishes in which microdrops of medium are arranged with each dish containing approximately 100 µl drops (TL Hepes with $Ca^{2+}$ and $Mg^{2+}$) containing the oocytes and 20 µl drops (TL Hepes with $Ca^{2+}$ and $Mg^{2+}$ and 20–50% fetal calf serum) to one side containing the cultured ICM cells. The addition of between 1 and 75% fetal calf serum, commonly 30%, or other sera with activity similar to fetal calf serum, to the medium is beneficial in reducing the attraction, i.e., the adhesiveness, of the stem cells, thereby preventing cell agglutination and allowing easier handling during micromanipulation.

The micromanipulation process involves a cell holding pipette having an outer diameter of approximately 120–180 µm and an inner diameter of approximately 25–35 µm, and a beveled, sharpened enucleation and transfer micropipette having an outer diameter of approximately 10 to 45 µm, depending upon the size of the stem cell. The oocyte is positioned on the holding pipette so that the polar body is towards the transfer tip. A small amount of cytoplasm from the region directly beneath the polar body is removed. The transfer tip is retracted from the zona pellucida and the cytoplasm ejected. The tip is reinserted through the same hole and an ICM cell is deposited beneath the zona pellucida. The cell is pressed against the cytoplasm where it sticks firmly to the cytoplasmic membrane. Due to the adhesion of the cells, transfer pipettes are changed frequently.

Cell Fusion

A variety of fusion techniques may be employed for this invention. For example, the onset of the electroporation by electrofusion can induce the fusion process. Electrofusion is accomplished by providing a pulse of electricity that is sufficient to cause a transient breakdown of the plasma membrane. This breakdown of the plasma membrane is very short and the membrane reforms very rapidly. If two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,994,384 to Prather et al., which is incorporated herein by reference, for a further discussion of this process. A variety of electrofusion media can be used including sucrose, mannitol, sorbitol and phosphate buffer solution.

Fusion can also be accomplished using Sendai virus as a fusigenic agent (Graham, 1969).

Polyethylene glycol (PEG) may also be used as a fusigenic agent. Under prescribed conditions, PEG provides excellent fusion results. In one protocol, the cells are fused in PEG (molecular weight 1,300–1,600 Sigma), which is mixed in a solution containing TL Hepes (approximately 1:0.25 µg/ml) and PVA (approximately 1 µg/ml). The media containing the cells is then passed through one or more dilutions (approximately 1:1) of the above-described PEG media. The nuclear transfer embryos are then allowed to rest in a culture media, such as TL Hepes containing fetal calf serum until the cell membranes return to a normal appearance. To activate the embryos, the embryos are washed in $Ca^{2+}$ and $Mg^{2+}$-free TL Hepes and exposed to an ionophore, for example, Ionomycin (Calbiochem). This is followed by another rest in TL Hepes containing fetal calf serum, after which the embryos are returned to a maintenance medium such as CR1aa. Experimental conditions will vary depending upon the products used.

The techniques incorporated herein proved to be successful in producing blastocysts that, when transferred to cattle, were capable of establishing pregnancies.

Microinjection

Because the ES cells are much smaller in relative size to the enucleated oocyte, the ES cells can be micro-injected directly into the cytoplasm of the enucleated oocyte as was done for ICM cells of the mouse by Illmensee and Hoppe (1981).

Gene Transfer

The ability to derive and multiply in culture bovine embryonic stem cells and the ability to make offspring from the cultured cells by nuclear transfer provides the technology required to use existing technology to efficiently transfer genes into bovine embryos, to select only the transgenic ES cells, and to be site specific in the genomic site of gene introduction or deletion.

In practice, genes can be transferred into bovine ES cells during their culture by either electroporation and transfection, techniques commonly used on other cell types, by direct microinjection, or by viral vector. Most commonly used viral vectors have been shown non-infectious to cultured bovine cells. However, Kim (1992) reports the development of a vector which infects genes into bovine embryonic cells. Another method for genetic transformation of organisms is by accelerated particle mediated transformation as described in U.S. Pat. No. 5,120,657 to McCabe et al., which is incorporated herein by reference.

The introduced gene construct would contain DNA sequences for a selectable marker such as resistance to neomycin and sequences coding for known homologous sequences in the bovine genome. The later provides site specificity for targeting gene insertion or with appropriate antisense or ribozyme construct addition, it also provides a method for site specific deletion of DNA sequences or a gene.

ES cells so constructed and surviving neomycin or other selectable marker treatment would be selected for use as nuclear donor cells in nuclear transfer with the expectation that all of the embryos resulting from the nuclear transfer would have integrated the introduced DNA into their genome. Blastocysts resulting from this nuclear transfer would be transferred into cows and developed in utero to offspring with the expectation that all would be transgenic.

Conventional techniques for producing transgenic animals result in less than 10% of the pronuclear stage embryos microinjected with DNA becoming born offspring and less than 10% of these being transgenic (Rexroad, 1992). The use of transgenic ES cells as donors in nuclear transfer increases the efficiency of gene transfer and reduces the cost of cow maintenance considerably even though only 15–30% of the cows receiving nuclear transfer derived embryos are expected to complete gestation.

The present invention also has utility in transferring genes into embryos by microinjection of DNA into cultured ES cells, which can then be used to form the germ cells of an embryo. Reference is made to Ebert and Selgrath, 1991, for a review of this discussion as it applies to the transfer of genes into embryos by microinjection of DNA into the pronucleus of an egg. Use of the ES cell gene transfer method and the selection of cultured cells for homologous recombination between an introduced and native gene sequence allow gene insertion or deletion at specific chromosome sites, which could be used for correcting genetic defects or for adding new genes. The animals that incorporate the foreign gene are termed transgenic.

Embryonic stem cells are dissociated from each other and cultured as described above. The ES cell is then injected with copies of a foreign gene using standard microinjection technology (Ebert and Selgrath, 1991). The ES cells are then transferred into a recipient oocyte as described above, fused, and transferred to a recipient female as soon as possible to minimize the deleterious effects of long-term culture on embryo stability.

Analysis of gene incorporation can be performed using a probe which is specific for the gene injected. Those animals determined to be transgenic can then be used to develop a new line of transgenic animals.

There is no limitation on the gene which may be transferred by the method of this invention. Growth hormone genes may be used to enhance growth rate, increase the efficiency of food utilization, increase lactation, or reduce fat on carcasses. The gonadotrophin releasing hormone gene may be used for biosterilization. Synthetic genes encoding antigenic proteins may be used to assure heightened immune response. Lymphokine genes may have value in enhancing resistance to viruses, tumors and other challenges. Gonadotrophin genes may be used to enhance ovulation and increase fertility. Genes regulating fatty acid synthetase or lipase production may be used to affect the lipid content of animal products. The genes transferred may be of genomic, cDNA, synthetic or mixed origin, and of natural or modified sequence.

The following examples are offered by way of illustration and not by way of limitation.

EXPERIMENTAL PROCEDURES

Experiment 1

Effect of Various Culture Media Components on Survival and Mitosis of Bovine Embryonic Stem Cells The following experiment was designed to compare the effects of various growth factors, media, and media supplements on cell maintenance and growth rates of bovine ES cells. Several mitotic or differentiation inhibiting factors were tested in various media combinations for their ability to promote prolonged mitotic activity of ES cells cultured in loose suspension.

Preliminary experiments revealed that bovine ES cells grown on feeder layers of mouse STO fibroblast cells, with or without differentiating inhibitory activity (DIA) (Am Rad Corp., Esgrow), quickly differentiated primarily into epithelial cells. DIA is the active component of Leukemia Inhibitory Factor (LIF) or Differentiating Inhibitory Factor (DIF) of mouse fibroblast or BRL cells, which prevents differentiation of mouse ES cells.

To prevent differentiation, ES cells were cultured in suspension at a concentration sufficiently low (1,000–1500 cells/10 $\mu$l drop) so that cell aggregation and differentiation did not occur. Cell aggregation, a prerequisite for differentiation, was prevented in all cultures if the cells were diluted by making new culture drops every 4 to 5 days such that the concentration of cells never exceeded 1,500 per 10 $\mu$l drop. Cell viability was determined by staining with propidium iodide.

Numerous experiments utilizing cells derived from embryos cultured under standard mouse embryonic stem cell conditions, including the addition of differentiation inhibiting factors, as donors for nuclear transfer have not resulted in any development. These cell lines represent tissues isolated from putative trophectoderm, fibroblast, endothelium and epithelium origin, and grown on various feeder layer cell types. Over 400 nuclear transfer embryos were created with the furthest development only to the 12-cell stage in two embryos. It was concluded from these experiments that culture under these conditions did not prevent differentiation, and that these cells were not capable of directing embryonic growth when transferred into an enucleated oocyte.

The choice of the preferred culture media was the result of a set of four experiments whereby three or four media were tested for ability to maintain cell growth and viability after one month in culture. Ten ml samples of the media were prepared with the components listed in the following table. A sufficient amount of CR1aa (or CR1 in medium 5 or TCM-199 in medium 8) was added to each medium to make up a 10 ml sample:

| Medium | Components |
| --- | --- |
| 1 | CR1aa + SIT[1] + FCS[2] |
| 2 | CR1aa + SIT[1] + DIA[3] |
| 3 | CR1aa + SIT[1] + EGF[4] |
| 4 | CR1aa + SIT[1] + glucose[5] |
| 5 | CR1 + DMEM$_{aa}$[6] + FCS[2] |
| 6 | CR1aa + SIT[1] + Rifampicin[7] |
| 7 | CR1aa + SIT[1] + CR Laminin[8] |
| 8 | TCM-199 + FCS[2] |
| 9 | CR1aa + SIT[1] + BRL[9] |
| 10 | CR1aa + SIT[1] + UCM[10] |

[1] 1 μl/ml of a standard selenium (sodium selenite), insulin, transferrin medium (Sigma I 1884)
[2] 5% (v/v) fetal calf serum
[3] 1 μg/ml (AmRad Corp., Esgrow)
[4] 1 μg/ml Epidermal Growth Factor
[5] 3 mM glucose
[6] 100 μl DMEM$_{aa}$/10 ml CR1
[7] 5 μl/ml
[8] 100 μl CR Laminin/10 ml CR1aa
[9] 50:50 dilution of BRL conditioned medium (ATCC CRL 1442)
[10] 50:50 dilution of Uterine Conditioned Medium Under these conditions the media factors differed considerably in their ability to support and promote ICM cell proliferation.

The results are shown in FIGS. 1–4.

Only media consisting of CR1aa plus SIT and either glucose, rifampicin, laminin, or 5% fetal calf serum supported mitosis through 2 to 3 weeks of culture.

Of these only CR1aa plus SIT plus 5% FCS allowed mitosis and continued proliferation of ICM cells through 4 weeks and in several cultures to 2 months of culture. Although the CR1aa+SIT+5% FCS is probably not the only media capable of sustaining prolonged growth in culture, it was sufficiently acceptable to allow continuation into the nuclear transfer phase of the experiments.

Replacement of fetal calf serum with DIA, BRL conditioned media, α-fetoprotein, uterine cell conditioned media, or EGF, or replacement of SIT with DMEMaa or TCM-199 all resulted in no proliferation and loss of the cultures by days 12 to 22.

Figure 5:
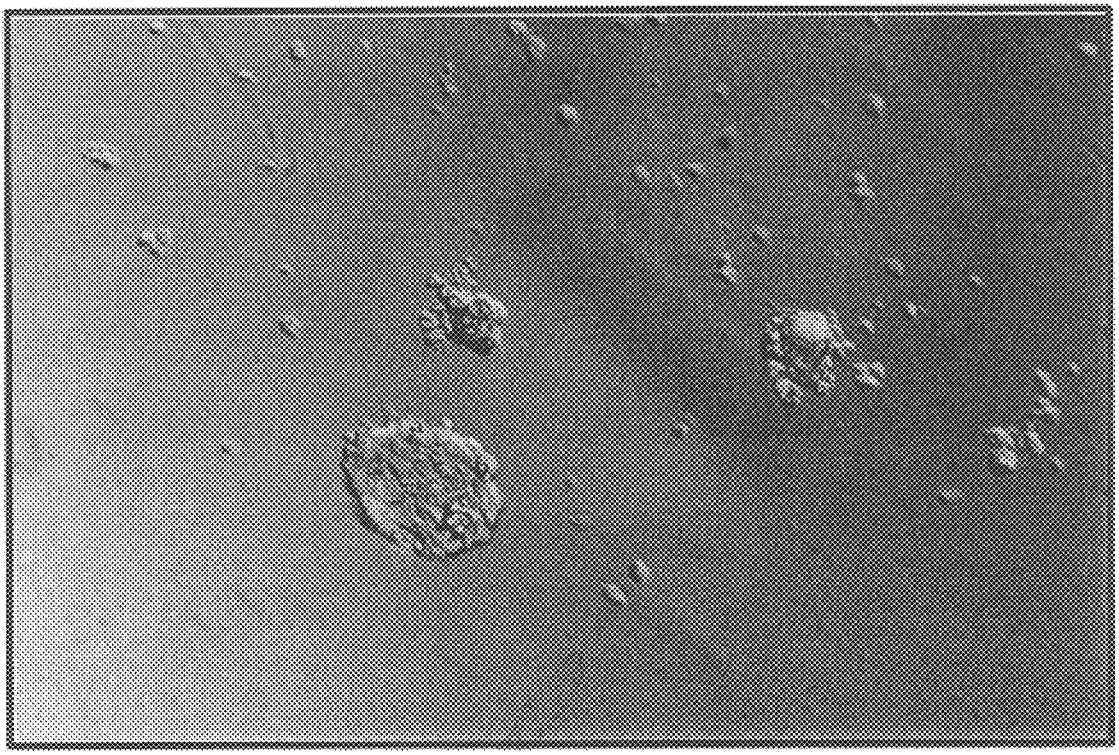
FIG. 5 is a photograph showing the ES cells cultured in Experiment 1.
Figure 6:
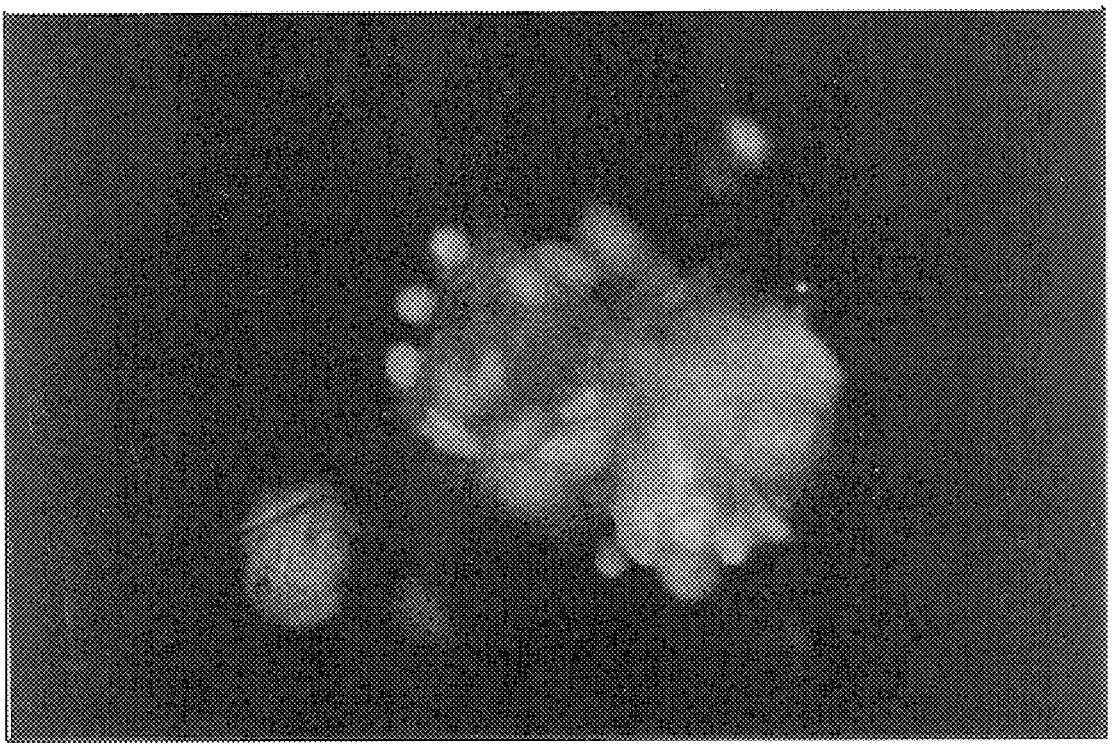
FIG. 6 is a photograph showing the aggregation of cultured ES cells.

From FIGS. 1–4, it can be seen that ES cells from day 9 and 10 bovine blastocyst can multiply in culture when cultured in CR1aa plus SIT and 5% FCS and that the cells multiply in culture to numbers as great as 1,000 after 3–4 weeks. These cells have the appearance of mouse embryonic stem cells, being small cells with large nuclei and little cytoplasm as illustrated in FIG. 5. When removed from nondifferentiating conditions and allowed to aggregate, the cultured cells formed embryoid bodies with the appearance of surrounding trophoblast and blastocoele cavity as illustrated in FIG. 6. When allowed to aggregate, the cells exhibited the synchronous beating heart activity often seen with mouse embryoid bodies.

Experiment 2

Use of Bovine ES Cells in Nuclear Transfer Embryos:

All embryos used in this experiment were in vitro derived from slaughterhouse bovine ovaries and frozen semen using the methods described by Sirard et al, 1988, Parrish et al, 1989, and Rosenkrans et al, (1990), which are incorporated herein by reference.

Oocyte Maturation:

Oocyte maturation was in TCM-199 containing 10% fetal calf serum (FCS) and NIH ovine Lutenizing Hormone (LH) 0.5 mg/ml (NIADDK-OLH-25).

Oocyte Fertilization:

Oocytes were fertilized using sperm from any one of 4 different bulls with sperm concentration and heparin dose adjusted for each bull.

Embryo Culture:

At 40–48 hrs post fertilization, embryos were manually stripped of all cumulus cells and extraneous sperm by repeated pipetting through a 190μ fire polished pipette. Subsequent embryo culture was carried out in CR1aa medium (Rosenkrans et al 1990, 1991) for 7 to 8 days at 39° C. in 5° $CO_2$ in air with high humidity until the embryos had hatched or were fully expanded after which they were subjected to immunosurgery. Embryos were first washed in 3 ml TL Hepes with PVA (1 mg/ml) (Sigma P-8136) and PVP (1 mg/ml) (Sigma PVP-40), then washed, through four to five $CO_2$ equilibrated microdrops (50 μl) of CR1aa with PVA (1 mg/ml) and PVP (1 mg/ml) under paraffin oil.

Rabbit anti-bovine antibody (1:10 dilution, Sigma B8270) was added at a 1:10 dilution for a final concentration of 1:100. Embryos were returned to the 39° C. incubator for 30 minutes. The embryos were again washed through four to five fresh microdrops of medium. Then guinea pig complement (Sigma S-1639) was added to the embryos at 1:10 dilution from a 1:500 stock for a final dilution of 1:5000.

Removing the Zonae Pellucidae:

While in the presence of complement, the zonae pellucidae were removed by manual pipetting through a non-fire polished 150μ pipette tip.

Separating the Cells from the Inner Cell Mass:

Isolated inner cell masses were again washed, then placed 1–3 ICMs per 10 μl drop of the medium CR1aa plus SIT (sodium selenite, insulin and transferrin, Sigma I 1884) and 5% (v/v) FCS under paraffin oil. Within five days, the ICMs started dissociating from a ball of cells into individual free floating cells. The medium was changed every 2–3 days by aspiration and replaced with fresh $CO_2$ equilibrated CR1aa with SIT and 5% (v/v) FCS. The addition of 5% FCS to the medium was beneficial in reducing the "stickiness" of these cells, allowing easier handling during micromanipulation. The ICM cells were maintained as disassociated cells in suspension culture for periods ranging from 1 week to 3 months, depending on the experimental protocol. Some cell lines were allowed to aggregate to test pluripotency. The ability of these aggregated cells to form simple to complex embryoid bodies indicates pluripotency.

The culture conditions were derived from Experiment 1. Cell viability was determined by staining with propidium iodide. All embryos used to make cell lines were derived from embryos cultured in the CR1aa+5% FCS media. The cultured non aggregated ICM cells were used as nuclear donor cells in nuclear transfer.

Nuclear Transfer
Maturation of Recipient Oocytes:

Recipient oocytes were matured in vitro (Sirard et al 1988) and stripped of cumulus at 16–18 hrs after initiation of oocyte maturation, using hyaluronidase at a concentration of 2 mg/ml and a fire polished pipette. oocytes were selected for presence of polar bodies and returned to maturation medium for another 2 to 4 hours.

Nuclear transfer was begun approximately 20 hours after oocytes were placed into culture when they were at metaphase II.

Transfer of ICM cells to Oocyte:

Manipulation was performed using a Nikon Diaphot microscope equipped with Hoffman Modulation Contrast optics and Narshige micromanipulators. Manipulation was done in culture dishes in which microdrops of medium were arranged with each dish containing 100 μl drops (TL Hepes with $Ca^{2+}$ and $Mg^{2+}$) containing the oocytes and 20 μl drops (TL Hepes with $Ca^{2+}$ and $Mg^{2+}$ and 20–50% FCS) to one side containing the cultured ICM cells. This was done to prevent the cells from sticking to the oocytes and to prevent mistaking ICM cells with any remaining cumulus cells.

Approximately 10 ES cells were picked up into the transfer pipette, then the tips were moved to the drop containing the oocytes. The cells were drawn higher into the pipette to allow space for enucleation of the oocyte. The oocyte was positioned on a holding pipette so that the polar body was towards the transfer tip. A small amount of cytoplasm from the region directly beneath the polar body was removed. The transfer tip was retracted from the zona and the cytoplasm ejected. The tip was reinserted through the same hole and an ICM cell was deposited beneath the zona. The cell was pressed against the cytoplasm where it stuck firmly to the cytoplasmic membrane. Due to the extreme stickiness of the cells, transfer pipettes were changed frequently.

Nuclear transfer was completed by 24 hrs, and the unfused units were placed in CR1aa medium overnight. All fusion was done with oocytes at 42 hr post follicular removal.

Fusion:

Fusion was accomplished with the use of polyethylene glycol. The protocol used PEG, (MW 1300–1600, Sigma) 1:0.25 gm/ml in TL Hepes w/PVA 1 mg/ml and PVP 1 mg/ml for 45 sec followed by a 1:1 dilution in the same media for 1 min., then another 1:1 dilution for 2 min, then a final 1:1 dilution for 2–3 min. The most reliable PEG was from Boehringer-Mannheim Biochemical (PEG MW 1500). A 15 minute rest in TL Hepes containing 20% FCS allowed membranes to return to a normal appearance.

To activate, the embryos were washed through $Ca^{2+}$ and $Mg^{2+}$-free TL Hepes then exposed to 5 mM Ionomycin (Calbiochem 407950) in 1 ml of media for 45 sec. This was followed by another 15 min rest in TL Hepes containing 20% FCS, after which embryos were returned to CR1aa medium for further maturation. This technique proved to be successful in producing blastocysts that, when transferred to cattle, were capable of establishing pregnancies.

RESULTS

One way of accurately determining totipotency of embryonic cells is to fuse the cell in question into an enucleated metaphase II oocyte. Table 1 illustrates the results from the derivation and use of cells from 12 bovine embryonic stem cell lines in nuclear transfer.

TABLE 1

Use of Bovine Embryonic Stem Cells in Nuclear Transfer to Produce Blastocysts

| Cell Line | Days PIS[1] to Nuclear Transfer | Cleavage (%) | | Nuclear Transfer Clones Made[2] | Blastocysts[3] (No.) | Blastocysts % of Clones[4] | Blastocysts % of Cleavage |
|---|---|---|---|---|---|---|---|
| 6-18 | 35 | 14/24 | (58) | 24 | 6 | 25 | 43 |
| 6-25 | 42 | 20/32 | (63) | 32 | 4 | 12.5 | 20 |
| 7-9 |  | 21/33 | (64) | 33 | 4 | 12 | 19 |
| 9-17 | 17 | 71/92 | (77) | 92 | 19 | 21 | 27 |
| 12-10 | 71 | 18/22 | (82) | 22 | 4 | 18 | 22 |
| 10-1 | 101 | 15/22 | (61) | 22 | 4 | 18 | 27 |
| 1-24 | 6 | 36/44 | (82) | 44 | 9 | 20 | 25 |
|  |  | 2/33 | (6) | 33 | 0 | 0 | 0 |
| 1-24 | 13 | 43/57 | (75) | 57 | 11 | 19 | 26 |
| 1-24 | 20 | 20/42 | (48) | 42 | 6 | 14 | 30 |
| 1-24 | 27 | 61/74 | (82) | 74 | 12 | 16 | 20 |
| 2-28 | 14 | 17/23 | (74) | 23 | 4 | 17 | 24 |
|  |  | 4/5 | (80) | 5* | 2 | 40 | 50 |
| 3-6 | 21 | 40/47 | (85) | 47 | 4 | 8.5 | 10 |
| 2-27 |  | 21/28 | (75) | 28 | 6 | 21 | 29 |
| 4-30** | 54 | 21/39 | (54) | 39 | 6 | 15 | 29 |
| 5-1** | 61 | 36/42 | (86) | 42 | 8 | 19 |  |
| TOTAL |  | 460/659 | (70) | 659 | 109 | 15% | 25% |

[1]PIS = days Post Immunosurgery. Trophoblast cells were removed and culture of inner cell mass cells initiated.
[2]Each clone is the product an attempted fusion of an inner cell mass cell with an enucleated oocyte.
[3]The number of blastocysts after in vitro culture of the clones for 7 days.
[4]The frequency of clones becoming blastocysts after 7 days of culture.
*All nuclear transfers were performed with fusion and activation at 42 hr, except the 5 clones noted by the *, which were fused at 24 hr and activated at 42 hr.
**All cell lines were derived from the pooled inner cell mass of three blastocysts, except lines 4-30 and 5-1, which were each derived from the inner cell mass of a single blastocyst.

The cell lines ranged from 6 to 101 days of culture at the time of nuclear transfer. A total of 659 embryos (clones)

were made by nuclear transfer. After culture for 7 days in vitro in CR1aa and SIT plus 5% FCS 109 became blastocysts (15%). Each cell line was derived from the inner cell masses of 3 blastocysts except cell lines 4-30 and 5-1 which were each derived from the inner cell mass of a single blastocyst. The frequency of blastocysts after nuclear transfer did not differ from the mean of the other 10 cell lines. Cell line 1-24 was used for nuclear transfer after culture for either 13, 20, or 27 days. The frequency of ICM cells becoming blastocysts after nuclear transfer did not differ over duration of culture as illustrated in Table 2. Cells from line 10-1 were equally effective in producing blastocysts after 101 days of culture.

TABLE 2

Day 7 Blastocysts Derived from Use of ES Cells in Nuclear Transfer

| Days Post[1] Immunosurgery | No. of Cell Lines | Blastocysts/ Fused NT | Blastocysts, % |
| --- | --- | --- | --- |
| 0–14 | 4 | 26/102 | 26 |
| 15–28 | 5 | 47/213 | 22 |
| 29–42 | 2 | 14/55 | 25 |
| 42–56 | 1 | 6/21 | 29 |
| 57–70 | 1 | 8/36 | 22 |
| 71–84 | 1 | 4/18 | 22 |
| 99–112 | 1 | 4/15 | 27 |

[1]Days post-immunosurgery at the time of nuclear transfer.

Totipotency of ES cells from 2 cultured cell lines was determined by transfer of blastocysts derived from ES cell nuclear transfer into recipient cells.

The results presented in Table 3 show that at least some of the ICM cells retain totipotency after culture.

TABLE 3

Use of Bovine Embryonic Stem Cells in Nuclear Transfer to Produce Fetuses

| Cell Line[1] | Days PSI to transfer[2] | No. blastocysts/ no. clones made[3] | No. blastocysts transferred into cows | No. cows pregnant at | No. blastocysts surviving as fetuses in uterus at gestation days | | | | |
| --- | --- | --- | --- | --- | --- | --- | --- | --- | --- |
| | 120 | | | | 42 days | 42 | 56 | 70 | 150 | 180 |
| 10-1 | 101 | 4/22 | 4/4 | 3/4 | 1 | 0 | — | — | — | — |
| 1-24 | 6 | 9/44 | 9/6 | 4/6 | 5 | 5 | 5 | 4 | 2 | 2 |
| 1-24 | 13 | 11/57 | 6/4 | 0/4 | 0 | — | — | — | — | — |
| 1-24 | 20 | 6/42 | 6/4 | 3/4 | 4 | 4 | 4 | 4 | 4 | 2 |
| 1-24 | 27 | 12/74 | 9/9 | 3/9 | 3 | 1 | 1 | 1 | 1 | 1 |
| TOTAL | | 34/27 | 13/27 49% | 13 | 10 | 10 | 9 27% | 7 21% | 5 14.7% |

[1]Each of these cell lines was established from the pooled inner cell masses of 3 blastocysts.
[2]PIS = days Post Immunosurgery and start of ICM cell cultures.
[3]The number of blastocysts developed per number of clones made after 7 days of culture.

The efficiency of blastocyst production from use of the cultured ICM cells in nuclear transfer (15%) is similar to the efficiency of using morulae cells as the donated nucleus in conventional nuclear transfer. (18%) Barnes et al 1990. Thirty four blastocysts derived from cell line 10-1 and from cell line 1-24 after culture for 6, 13, 20, or 27 days were transferred into uteri of 27 cows. Thirteen of the cows (49%) became pregnant and 5 (18.5%) are still carrying 5 (15%) fetuses with heart beats clearly imaged with ultrasononography at 180 days of gestation.

The ES cell culture system reported here prevents differentiation by culturing cells as a loose suspension with less than 1500 cells per 10 μl drop. Without cell-cell contact, neither cell aggregation or monolayer formation occur.

As shown in Table 4 these methods allow the establishment of stem cell lines from 30–50% of the blastocysts attempted.

TABLE 4

Efficiency of stem cell line production by bull

| Bull No. | No. of ICM Cultures Started | Percentage Established Cell Lines |
| --- | --- | --- |
| | | Cell lines attempted |
| Angus | 6 | 45–52% |
| 9805 | 8 | 23–34% |
| 9809 | 10 | 42–47% |
| 9813 | 5 | 50–57% |

It is to be understood that the present invention is not limited to the particular configuration of the apparatus and method of use disclosed in this application, but embraces such modified forms as come within the scope of the claims following the Bibliography.

BIBLIOGRAPHY

PCT Publication WO 09/03432 to Evans and Moor, entitled "Derivation of Pluripotent Embryonic Cell Lines From Domestic Animals."

U.S. Pat. No. 4,994,384 to Prather et al., entitled "Multiplying Bovine Embryos."

U.S. Pat. No. 5,096,822 to Rosenkrans. Jr. et al., entitled "Bovine Embryo Medium."

U.S. Pat. No. 5,120,657 to McCabe et al., entitled "Apparatus for Genetic Transformation."

Alberts, B., et al., Ed., 1989, *Molecular Biology of the Cell, Second Edition,* Garland Publishing, Inc., New York, pp. 859–863

Anderson, G. B., 1992, "Isolation and Use of Embryonic Stem Cells from Livestock Species," *Animal Biotechnology,* 3(1), 165–175.

Butler, J. E., et al., 1987, "Production of Ovine Chimeras by Inner Cell Mass Transplantation," *J. Animal Sci.,* 65:317–324.

Capecchi, M. R., 1989a, "The New Mouse Genetics: Altering the Genome by Gene Targeting," *Trends Genet.,* 5: 70–76.

Capecchi, M. R., 1989b, "Alternating the Genome by Homologous Recombination," *Science. N Y,* 244: 1288–1292.

Collas, P. and J. M. Robl, 1991, "Relationship Between Nuclear Remodelling and Development in Nuclear Transplant Rabbit Embryos," *Biol. Reprod.,* 45:455–465.

Doetschman, T. P., et al., 1988, "Establishment of Hamster Blastocyst-Derived Embryonic Stem (ES) Cells," *Dev. Biol.,* 127:224.

Ebert, K. M. and J. P. Selgrath, 1991, "Changes in Domestic Livestock Through Genetic Engineering," *Animal Applications of Research in Mammalian Development,* 4:233–266.

Evans, M. J., et al., 1990, "Derivation and Preliminary Characterization of Pluripotent Cell Lines from Porcine and Bovine Blastocysts," *Theriogenology,* 33:125.

Evans, M. J. and M. H. Kaufman, 1981, "Establishment in Culture of Pluripotent Cells from Mouse Embryos," *Nature,* 292:154.

First and Prather, 1991, "Genomic Potential in Mammals," *Differentiation,* 48:1–8.

Gossler, A., et al., 1986, "Transgenesis by Means of Blastocyst-Derived Embryonic Stem Cell Lines," *Proc. Natl. Acad. Sci.,* 83:9065.

Graham, C. F., 1969, "The Fusion of Cells with One and Two Cell Mouse Embryos," *Wistar Inot. Symp Monogr.,* 9:19.

Hansel, W. and R. A. Godke, 1992, "Future Prospectives on Animal Biotechnology," *Animal Biotechnology* 3(1), 111–137.

Hooper, M., et al., 1987, "HPRT-Deficient (Lesch-Nyhan) Mouse Embryos Derived from Germ Line Colonization by Cultured Cells," *Nature,* 326:292.

Illmensee, K. and P. C. Hoppe, 1981, "Nuclear Transplantation in Mus musculus: Developmental Potential of Nuclei from Preimplantation Embryos," *Cell,* 23:9–18.

Joyner, A. L., 1991, "Gene Targeting and Gene Trap Screens Using Embryonic Stem Cells: New Approaches to Mammalian Development," *Bioassays,* 13(12):649–658.

Kim, T., 1992, "A study of Retrovirus-Mediated Gene Transfer in Bovine Embryos," Ph.D. Thesis, University of Wisconsin-Madison.

Koller, B. H., et al., 1989, "Germ Line Transmission of a Plasmid Alteration Made in a Hypoxanthine Phosphoriboxyl Transferase Gene by Homologous Recombination in Embryonic Stem Cells," *Proc. Natl. Acad. Sci.,* 86:8927.

Kono, T., et al., 1991, "Development of Enucleated Mouse Oocytes Reconstituted with Embryonic Nuclei," *J. Reprod. Fert.,* 93:165–172.

Lovell-Badge, R. H., et al., 1987, "Tissue Specific Expression of the Human Type II Collagen Gene in Mice," *Proc. Natl. Acad. Sci.,* 84:2803.

McGrath, J. and D. Solter, 1983, "Nuclear Transplantation in the Mouse Embryo by Microsurgery and Cell Fusion, *Science,* 220:1300.

Modlinski, J. A., et al., 1990, "Nuclear Transfer from Teratocarcinoma Carcinoma Cells into Mouse Oocytes and Eggs," *Development,* 108:337–348.

Moreau, J. F., et al., 1988, "Leukaemia-inhibiting Factor is Identical to the Myeloid Growth Factor, Human Interleukin for DA Cells," *Nature, Lond.* 336: 690–692.

Nagy, A., et al., 1990, "Embryonic Stem Cells Alone Are Able to Support Fetal Development in the Mouse," *Development,* 110:815–821.

Navara, C. S., et al., 1992, "Timing of Polarization in Bovine Embryos and Developmental Potential of Polarized Blastomeres (Abst. 82), *Soc. Study of Reprod.—Suppl.* 1, 46:71.

Notarianni, E., et al., 1990, "Derivation of Pluripotent, Embryonic Cell Lines from Porcine and Ovine Blastocysts," *Proc. 4th World Cong. Genetics Applied to Livestock Production XIII,* 58–64.

Notarianni, E., et al., 1991, "Derivation of Pluripotent, Embryonic Cell Lines from the Pig and Sheep," *J. Reprod. Fert. Suppl.* 43:255–260.

Piedrahita, J. A., et al., 1988, "Isolation of Embryonic Stem Cell-Like Colonies from Porcine Embryos," *Theriogenology,* 29:286.

Prather, R. S. and J. M. Robl, 1991, "Cloning by Nuclear Transfer and Embryo Splitting in Laboratory and Domestic Animals," *Animal Applications of Research in Mammalian Development,* 4:205–232.

Rexroad, C., 1992, "Transgenic Technology in Animal Agriculture," *Animal Biotechnology,* 3(1), 1–13.

Rossant, J. & A. L. Joyner, 1989, "Towards a Molecular Genetic Analysis of Mammalian Development," *Trends Genet.,* 5: 277–283.

Saito, S., et al., 1992, "Bovine Embryonic Stem Cell-Like Cell Lines Cultured Over Several Passages," *Roux's Arch. Dev. Biol.,* 201:134–141.

Smith, A. G., et al., 1988, "Inhibition of Pluripotent Embryonic Stem Cell Differentiation by Purified Polypeptides, *Nature,* 336:688.

Smith, L. C. and I. Wilmut, 1989, "Influence of Nuclear and Cytoplasmic Activity on the Development in vivo of Sheep Embryos after Nuclear Transplantation," *Biol. Reprod.,* 40:1027–1035.

Stanton, B. R., et al., 1990, "Germ-Line Transmission of an Inactive N-myc Allele Generated by Homologous Recombination in Mouse Embryonic Stem Cells, *Mol. Cell. Biol.,* 10:6755.

Stewart, C. L., 1991, "Prospects for the Establishment of Embryonic Stem Cells and Genetic Manipulation of Domestic Animals," *Animal Applications of Research in Mammalian Development,* Cold Spring Harbor Laboratory Press, New York, pp. 267–283.

Summers, P. M., et al., 1983, "Synthesis of Primary Bos taurus-Box Indicus Chimaeric Calves," *Animal Reprod. Sci.,* 6:91–92.

Williams, R. L., et al., 1988, "Myeloid Leukemia Inhibitory Factor Maintains the Developmental Potential of Embryonic Stem Cells," *Nature,* 336:684.

Wilmut, I., et al., 1991, "Genetic Manipulation of Mammals and its Application in Reproductive Biology," *J. Reprod. Fert.,* 92: 245–279.

Wilmut, I., et al., 1992, "Sources of Totipotent Nuclei Including Embryonic Stem Cells," *Proc. Symp. Cloning Mammals by Nuclear Transplantation,* 8–16.

Yagi, T., et al., 1990, "Homologous Recombination at c-fyn Locus of Mouse Embryonic Stem Cells with Use of Diphtheria Toxin A Fragment Gene in Negative Selection," *Proc. Natl. Acad. Sci.,* 87:9918.

What is claimed is:

1. A method for producing a bovine animal, the method comprising:

(a) providing a cultured bovine embryonic inner cell mass cell, wherein said inner cell mass cell has been cultured in a culture medium for a length of time sufficient for maintenance of said inner cell mass cell in an undifferentiated state;

(b) establishing an embryo from a nuclear transfer process, wherein said nuclear transfer process comprises the step of inserting said cultured bovine embryonic inner cell mass cell into an enucleated bovine oocyte, and the step of activating said embryo;

(c) implanting said embryo into a recipient bovine host; and (d) allowing said embryo to develop into the bovine animal.

2. The method of claim 1, wherein the step of inserting said cultured bovine embryonic inner cell mass cell into said enucleated bovine oocyte is accomplished by fusion.

3. The method of claim 1, further comprising the step of culturing said embryo in vitro or in vivo prior to implantation into a recipient bovine host.

4. The method of claim 3, wherein said embryo is cultured to a morula-stage embryo.

5. The method of claim 3, wherein said embryo is cultured to a blastocyst-stage embryo.

6. The method of claim 1, further comprising the step of introducing an exogenous gene into said cultured bovine embryonic inner cell mass cell of step (a).

* * * * *